(12) United States Patent
Syu

(10) Patent No.: US 10,039,435 B1
(45) Date of Patent: Aug. 7, 2018

(54) LARYNGOSCOPE HAVING ONE-ON-ONE WI-FI CONNECTING SYSTEM

(71) Applicant: JOHNFK MEDICAL CO., LTD., Pingtung County (TW)

(72) Inventor: Fei-Kai Syu, Pingtung County (TW)

(73) Assignee: JOHNFK Medical Co., Ltd., Pingtung County (TW)

( * ) Notice: Subject to any disclaimer, the term of this patent is extended or adjusted under 35 U.S.C. 154(b) by 0 days.

(21) Appl. No.: 15/659,821

(22) Filed: Jul. 26, 2017

(51) Int. Cl.
| | | |
|---|---|---|
| A61B 1/267 | (2006.01) | |
| A61B 1/00 | (2006.01) | |
| A61B 1/04 | (2006.01) | |
| H04N 5/225 | (2006.01) | |
| H04N 7/18 | (2006.01) | |

(52) U.S. Cl.
CPC ...... *A61B 1/00016* (2013.01); *A61B 1/00101* (2013.01); *A61B 1/04* (2013.01); *A61B 1/267* (2013.01); *H04N 5/2251* (2013.01); *H04N 7/185* (2013.01); *H04N 2005/2255* (2013.01)

(58) Field of Classification Search
CPC ... A61B 1/00016; A61B 1/00101; A61B 1/04; A61B 1/267; H04N 5/2251; H04N 7/185; H04N 2005/2255

USPC ........ 600/101, 104, 109, 110, 112, 114, 120, 600/121, 139, 143, 160, 185, 186, 188
See application file for complete search history.

(56) References Cited

U.S. PATENT DOCUMENTS

| | | | | |
|---|---|---|---|---|
| 5,333,603 A | * | 8/1994 | Schuman | A61B 18/24 600/108 |
| 5,941,818 A | * | 8/1999 | Hori | A61B 1/00073 600/110 |
| 2016/0296719 A1 | * | 10/2016 | Geraghty | A61M 16/0486 |
| 2016/0378939 A1 | * | 12/2016 | Baumberger | G06F 19/3412 705/2 |
| 2017/0169176 A1 | * | 6/2017 | Abiola | G06F 19/3418 |

* cited by examiner

*Primary Examiner* — Pedro Philogene
*Assistant Examiner* — David C Comstock
(74) *Attorney, Agent, or Firm* — Rosenberg, Klein & Lee

(57) ABSTRACT

The present invention relates to a laryngoscope having one-on-one Wi-Fi connecting system including a signal transmitter, a camera module, and a signal receiver, which is characterized to apply Wi-Fi direct transmission to transmit the image from the laryngoscope one-on-one to a display with security and stability effect that can prevent from any interference. Moreover, the invention also provides a bendable inspecting tube connected with the camera module, which can be bent to a desired shape easily for inspecting different sides of the patient that facilitates the diagnosis for doctors. It obtains the design effect of the invention.

3 Claims, 2 Drawing Sheets

LARYNGOSCOPE HAVING ONE-ON-ONE WI-FI CONNECTING SYSTEM

BACKGROUND OF THE INVENTION

The prior laryngoscope usually applies cables or wires to transmit image to a display. It is not convenient because of the heavy weight of the display and the interference of connecting cables and wires. Recently, an improved laryngoscope is provided with Bluetooth transmission function. But the transmission speed and distance of Bluetooth are poor that cannot provide high quality image. It is known that the transmission speed of Bluetooth is only about 723 Kbps and the transmission distance is less than 15 meters. The applied effect will be worse under actual environmental factor. Furthermore, the traditional inspecting tube of the laryngoscope is rigid, which includes a support made of metal or plastic, both of which being unbendable that might hurt patients when in use. Hence, the known design is not utilized and should be improved.

SUMMARY OF THE INVENTION

The present invention relates to a laryngoscope having one-on-one Wi-Fi connecting system mainly including a signal transmitter, a camera module, and a signal receiver, which is characterized to apply Wi-Fi direct transmission to transmit the image from the laryngoscope one-on-one to a display with security and stability effect that can prevent from any interference. Moreover, the invention also provides a bendable inspecting tube connected with the camera module, which can be bent to a desired shape easily for inspecting different sides of the patient that facilitates the diagnosis for doctors. Now, accompanying with drawings, the character and structure of the present invention will be disclosed as following.

DETAILED DESCRIPTION OF THE PREFERRED EMBODIMENT

Figure 1:
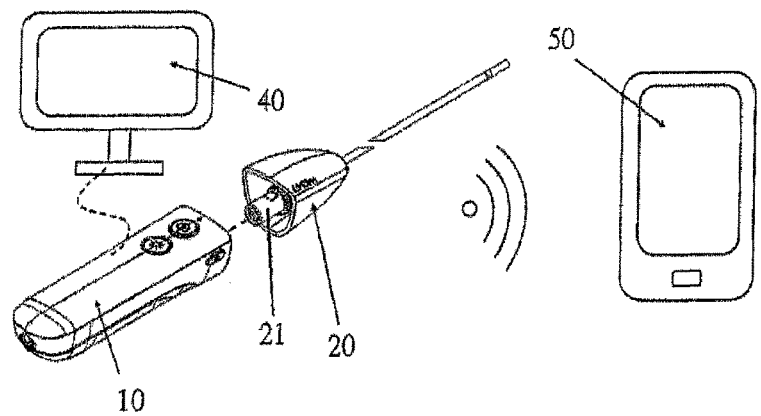
FIG. 1 is a perspective view of a laryngoscope having one-on-one Wi-Fi connecting system according to the present invention.
Figure 2:
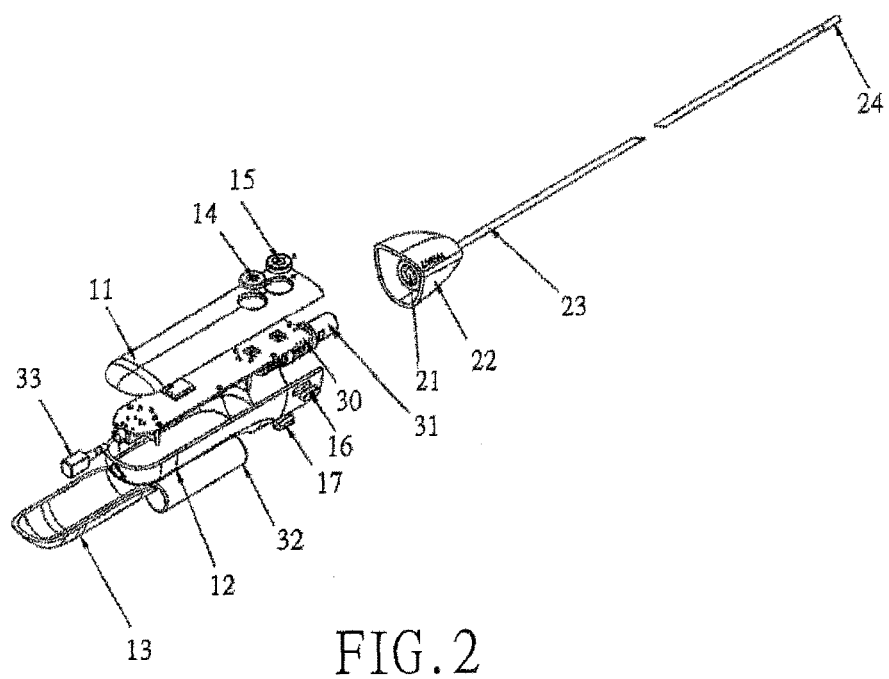
FIG. 2 is an exploded view of FIG. 1.

Please refer to FIGS. 1 and 2. The present invention relates to a laryngoscope having one-on-one Wi-Fi connecting system, which mainly includes a signal transmitter (10), a camera module (20), and a signal receiver (50). The signal transmitter (10) has an upper cap (11), a lower base (12), and a battery cover (13). An IC board (30) received in the signal transmitter (10) has its one end with a plug-end (31). The camera module (20) is composed of a shell (22), a socket-end (21), a bendable metal tube (23), and camera lens (24). The signal transmitter (10) and the camera module (20) are capable of being connected to become a completed single unit by use of easy connection between the plug-end (31) and the socket-end (21). After such connection, the camera lens (24) capture the image, which is then sent to the IC board (30). The IC board (30) transfers the image and transmits the signal to the receiver (50) under controlled by one-on-one Wi-Fi direct transmission. It is promised that the transmission of image will be stable and secure to prevent from most environmental interference or being stolen. Moreover, the bendable metal tube (23) is manufactured by a bendable metal stick winding with electrical wires of the camera module (20) and then coated with elastic medical polyamine ester. Hence, it can be bent to any desired shape for inserting into the throat of a patient for facilitating the inspection or observation. The doctor can thus diagnose more accurately and easily and prevents from injuring the patient when inspecting. Thus, it is to be understood that the present invention is effective and useful.

In application, the signal transmitter (10) has provided with at least three buttons including a power on-off button (16), a lighting button (14), and a camera control button (15). A connecting button (17) is also provided thereon that the signal transmitter (10) and the camera module (20) can be separated only when it is pressed. The battery cover (13) is sliding type for easily changing inner batteries.

Figure 3:
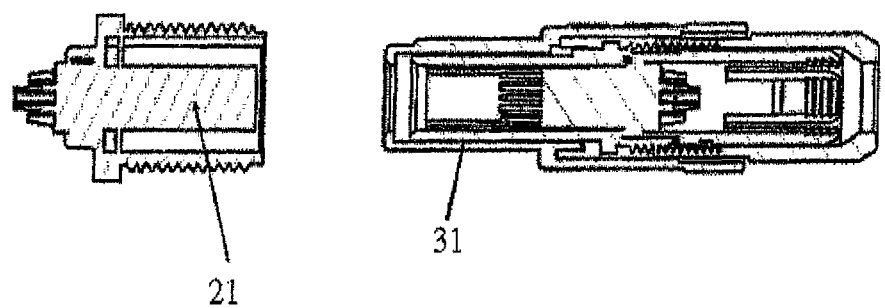
FIG. 3 is a cross-sectional plan view of the connecting means of the present invention.

As shown in FIG. 3, it can be found that the signal transmitter (10) and the camera module (20) can be separated easily. The camera module (20) is possible of being discarded and replaced with utility. The signal receiver (50) can received the single one-on-one Wi-Fi signal from the signal transmitter (10) by preset software. A pin hole (33) is provided at a tail end of the signal transmitter (10) for connecting a wire to a TV monitor (40) as a safe supplementary when the Wi-Fi transmission is not work.

What is claimed is:

1. A laryngoscope having a point-to-point Wi-Fi connecting system comprising:
    a signal transmitter, the signal transmitter configured to be external relative to a patient;
    a camera module; and
    a signal receiver;
    wherein the signal transmitter includes an upper cap, a lower base, a battery cover, and an IC board having a camera component and encapsulated by the upper cap and the lower base, and a first end of the signal transmitter being formed with a plug-end;
    wherein the camera module is adapted to be releasably coupled to the signal transmitter, the camera module including a socket-end and a light transmissible bendable metal tube configured for insertion into the patient, the light transmissible bendable metal tube having a distal end and a proximal end, the distal end having a camera lens mounted therein and the proximal end being coupled to the socket-end, the socket-end being releasably coupled to the plug-end for transmitting a captured optical image to the camera component of the IC board of the signal transmitter, the camera component thereby receiving light transmitted from the camera lens; and
    wherein the signal transmitter and the camera module are adapted to be connected into a single unit to form the releasable connection between the plug-end and the socket-end, the captured optical image received by the camera component being converted into an electrical signal, and the IC board transmitting the electrical signal to the signal receiver through the point-to-point Wi-Fi transmission.

2. The laryngoscope having the point-to-point Wi-Fi connecting system as claimed in claim 1, wherein the light transmissible bendable metal tube includes a bendable metal stick coated with elastic medical polyamine ester.

3. The laryngoscope having the point-to-point Wi-Fi connecting system as claimed in claim 1, wherein a pin hole is provided at a second end of the signal transmitter for receiving an electrical connector therein, the electrical connector being connected to a video cable of a TV monitor.

* * * * *